United States Patent [19]

Sikes et al.

[11] Patent Number: 4,868,287

[45] Date of Patent: Sep. 19, 1989

[54] INHIBITION OF MINERAL DEPOSITION BY POLYANIONIC/HYDROPHOBIC PEPTIDES AND DERIVATIVES THEREOF HAVING A CLUSTERED BLOCK COPOLYMER STRUCTURE

[75] Inventors: C. Steven Sikes, Mobile, Ala.; A. P. Wheeler, Clemson, S.C.

[73] Assignee: University of South Alabama, Mobile, Ala.

[21] Appl. No.: 88,247

[22] Filed: Aug. 24, 1987

[51] Int. Cl.$^4$ .................................................. C02F 5/10
[52] U.S. Cl. .................................... 530/324; 530/325; 530/326; 530/327; 530/328; 530/329; 530/330; 514/12; 514/13; 514/14; 514/15; 514/16; 514/17; 514/824; 514/901; 427/384; 424/49; 424/54; 433/215
[58] Field of Search ............................ 106/14.05, 14.15; 134/22.14; 210/698; 252/82, 175, 180; 433/215; 424/49, 54; 427/384; 514/12–17, 824, 901; 530/324–330

[56] References Cited

U.S. PATENT DOCUMENTS

| | | | |
|---|---|---|---|
| 4,339,431 | 1/1982 | Gaffar | 424/49 |
| 4,534,881 | 8/1985 | Sikes et al. | 252/175 |
| 4,585,560 | 4/1986 | Sikes et al. | 252/180 |
| 4,587,021 | 5/1986 | Wheeler et al. | 252/180 |
| 4,603,006 | 7/1986 | Sikes et al. | 252/180 |
| 4,643,988 | 2/1987 | Segrest et al. | 514/12 |

OTHER PUBLICATIONS

Hay, D. I. et al., Inorg. Persp. Biol. Med., 2, 271–285 (1979).
Hay, D. I. et al., Calcif. Tissue Int., 40, 125–132 (1987).

Primary Examiner—John Kight
Assistant Examiner—Frederick Krass
Attorney, Agent, or Firm—Oblon, Spivak, McClelland, Maier & Neustadt

[57] ABSTRACT

A poly-amino acid compound capable of inhibiting mineral deposition, which has the structure:

poly $(X)_n$ poly $(Y)_m$ where
each X is a residue independently selected from the group consisting of aspartic acid, glutamic acid, phosphoserine, phosphohomoserine, phosphotyrosine, and phosphothreonine,
each Y is independently a residue selected from the group consisting of alanine, leucine, isoleucine, valine and glycine,
n is 2 to 60,
m is 2 to 60, and
$n+m \geq 5$,
and wherein poly $(X)_n$ may contain up to 10% of the Y residues and poly $(Y)_m$ may contain up to 10% of the X residues, and salts thereof.

16 Claims, 9 Drawing Sheets

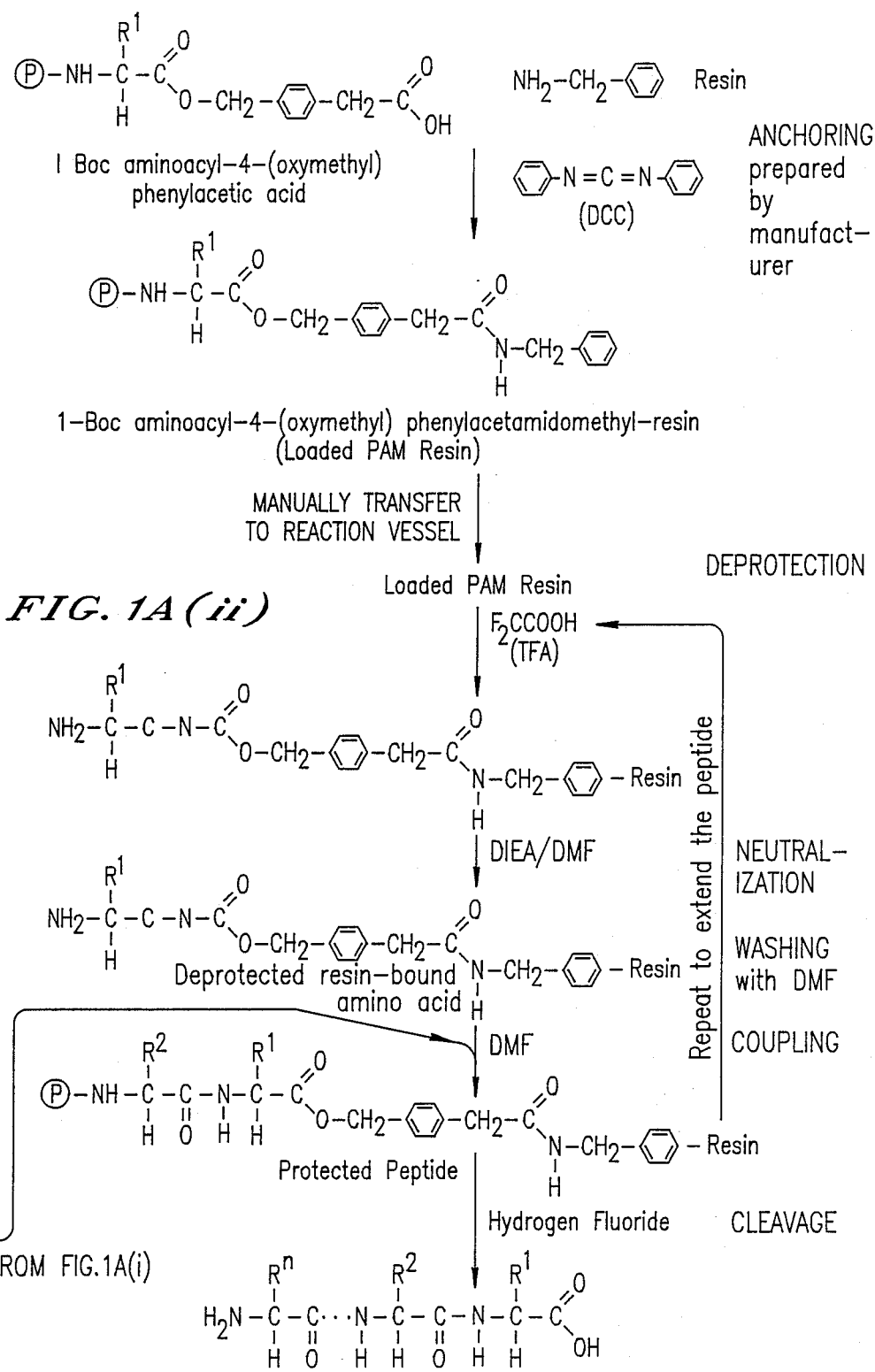
FIG. 1A (ii)

SOLID PHASE PEPTIDE SYNTHESIS

LEGEND:

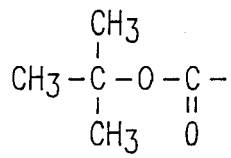   tert-Butyloxycarbonyl (t-Boc)

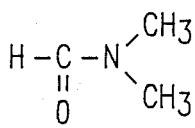

*FIG. 1B*

DCC   Dicyclohexylcarbodiimide
TFA   Trifluoroacetic acid
DCM   Dichloromethane
DMF   N,N-Dimethylformamide $$H-\underset{\underset{O}{\parallel}}{C}-N\begin{array}{c}CH_3\\CH_3\end{array}$$

DIEA  N,N-Diisopropylethylamine
      $[(CH_3)_2 CH]_2 NC_2H_5$ $R^1 ..... R^n$ Amino acid R groups protected until final cleavage Resin  Copoly (styrene – 1% – Divinylbenzene)

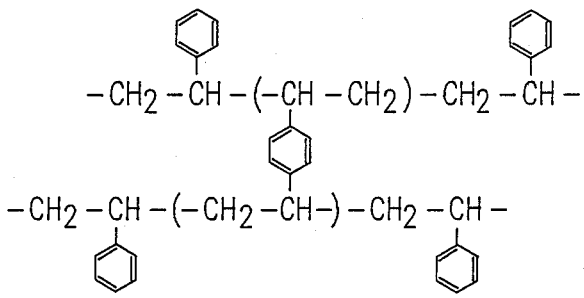

PAM   Phenylacetamidomethyl (organic linker)

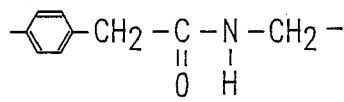

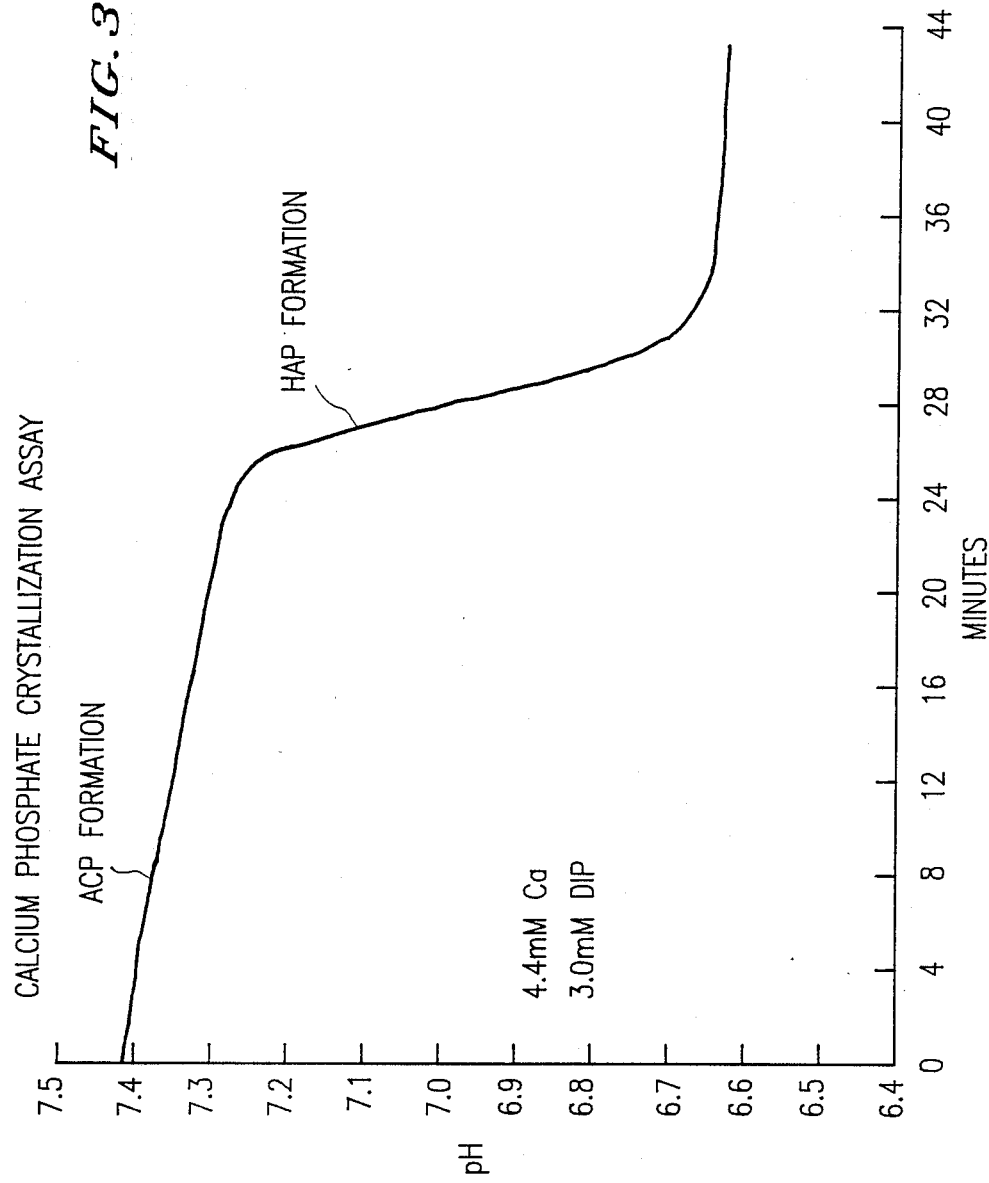

INHIBITION OF MINERAL DEPOSITION BY POLYANIONIC/HYDROPHOBIC PEPTIDES AND DERIVATIVES THEREOF HAVING A CLUSTERED BLOCK COPOLYMER STRUCTURE

Work for the present invention was supported in part by grants from the Alabama Research Institute, The National Science Foundation, and the National Oceanic and Atmospheric Administration (Sea Grant).

BACKGROUND OF THE INVENTION

1. Field of the Invention

The present invention relates to new peptides and polypeptides that are powerful inhibitors of mineral formation, for example, crystallization of calcium carbonate, calcium phosphate, calcium sulfate and others. The materials are also useful in protecting metallic surfaces from corrosion.

2. Discussion of Background

Biological mineralization is a fundamental process in nature. Formation of bones and teeth from calcium phosphate and formation of shells and reefs from calcium carbonate are but two examples of this process.

Unfortunately, mineral deposits also frequently occur where they are not wanted. In the body, mineral deposition may contribute to dental plaque, hardening of the arteries, various organ stones, and failure of prosthetic devices like implanted heart valves. In the marine environment, the biomineral structures may cause problems as in the case of barnacles growing on the hulls of ships, adding extra bulk and creating drag. In industry, mineral scale forms on surfaces of cooling towers and other devices preventing their proper operation as heat exchangers and frequently promoting localized corrosion.

Because of the problems associated with unwanted mineral deposition, much effort has been devoted to finding mineralization inhibitors, particularly in industry, that might be used to prevent harmful mineral formation.

Molecules for prevention of mineral deposition have ranged from simple ions like $Mg^{+2}$ (Pytkowicz, R. M., J. Geol. 73, 196-199 (1965)) and $PO_4^{3-}$ or pyrophosphate (Simkiss, K., Biol. Rev. 39, 487-505 (1964)) to more complex organic materials. Inhibition by simple ions is based on the ability of these ions to interfere with the orderly formation of the crystalline lattice of the mineral, such as $CaCO_3$. In addition, phosphate and polyphosphates have the property of protecting metallic surfaces by forming very thin films that cover potential sites of corrosion on the surfaces.

Phosphonates were introduced in the late 1960's (Ralston, U.S. Pat. No. 3,336,221 (1967)). These are small organic molecules with $PO_3$ groups attached directly to a central carbon atom via a covalent bond to phosphorus. The phosphonates are very effective inhibitors of crystallization that work by adsorbing to crystal surfaces. Hydroxyethylidene diphosphonate (HEDP) is perhaps the most widely used phosphonate, still among the most powerful inhibitors of $CaCO_3$ formation known.

Use of phosphonates has some disadvantages though. For example, phosphonates can be degraded during chlorination which in turn may lead to elevated phosphates and associated phosphate scales. Phosphonates themselves may also precipitate under common operating conditions. HEDP is an exceptionally effective inhibitor of crystal nucleation on a weight basis as shown by its effect on lengthening the induction period prior to crystal growth, but it is not at all effective at inhibiting crystal growth after it begins, (Sikes and Wheeler, CHEMTECH, in press (1987)).

More recently, as a result of continuing efforts to identify better inhibitors, polyacrylate and other polyanionic materials have been identified (Rohm and Haas Company, Technical Bulletin CS-513A (1985), Fong and Kowalski, U.S. Pat. No. 4,546,156 (1985)). In the 1980's, antiscaling and anticorrosion technology has been based increasingly on use of synthetic polymers under alkaline conditions. The current trend in synthetic polymer for water treatment is the use of random copolymers or terpolymers with alternating side groups of $COO^-$ with groups like OH, $CH_3$, $PO_3^{2-}$, $SO_3^{2-}$ etc.

A new approach to identifying mineralization inhibitors was disclosed by Sikes and Wheeler U.S. Pat. Nos. 4,534,881 (1985); 4,585,560 (1986); and 4,603,006 (1986) and Wheeler and Sikes, U.S. Pat. No. 4,587,021 (1986). In these patents, it was disclosed that proteins and polysaccharides extracted from biological minerals like oyster shells are strong inhibitors of crystallization. By studying the structure of the natural molecules, particularly the proteins, clues to the chemical nature required for activity of synthetic polyamino acids were obtained. Based on this, certain polyanionic polyamino acids including random copolymers of negatively charged residues and nonionic residues were identified as useful inhibitors.

Some other patents related to this invention are the following:

Gaffar, U.S. Pat. No. 4,339,431, discloses copolymers of glutamic acid and alanine which are used as anticalculus agents in dentifrices or mouthwashes. The copolymers disclosed therein are random copolymers.

Segrest et al, U.S. Pat. No. 4,643,988, discloses polypeptides having a non-clustered arrangement of anionic and hydrophic amino acids, which were used for treatment of atherosclerosis (perhaps by preventing deposition of certain minerals).

Buck, U.S. Pat. No. 4,362,713, is directed to compositions and methods for preventing attachment of dental plaque to the surface of teeth by the use of salts of certain maleic acid copolymers.

In spite of the above approaches to solving the problems of unwanted mineral deposition, there remains a strong need for a new and more powerful inhibitors of mineral deposition which could be used in the body, in a marine environment, or industrially.

BRIEF DESCRIPTION OF THE DRAWINGS

FIG. 3: Data obtained from a calcium phosphate crystallization assay.

SUMMARY OF THE INVENTION

Figure 1A:
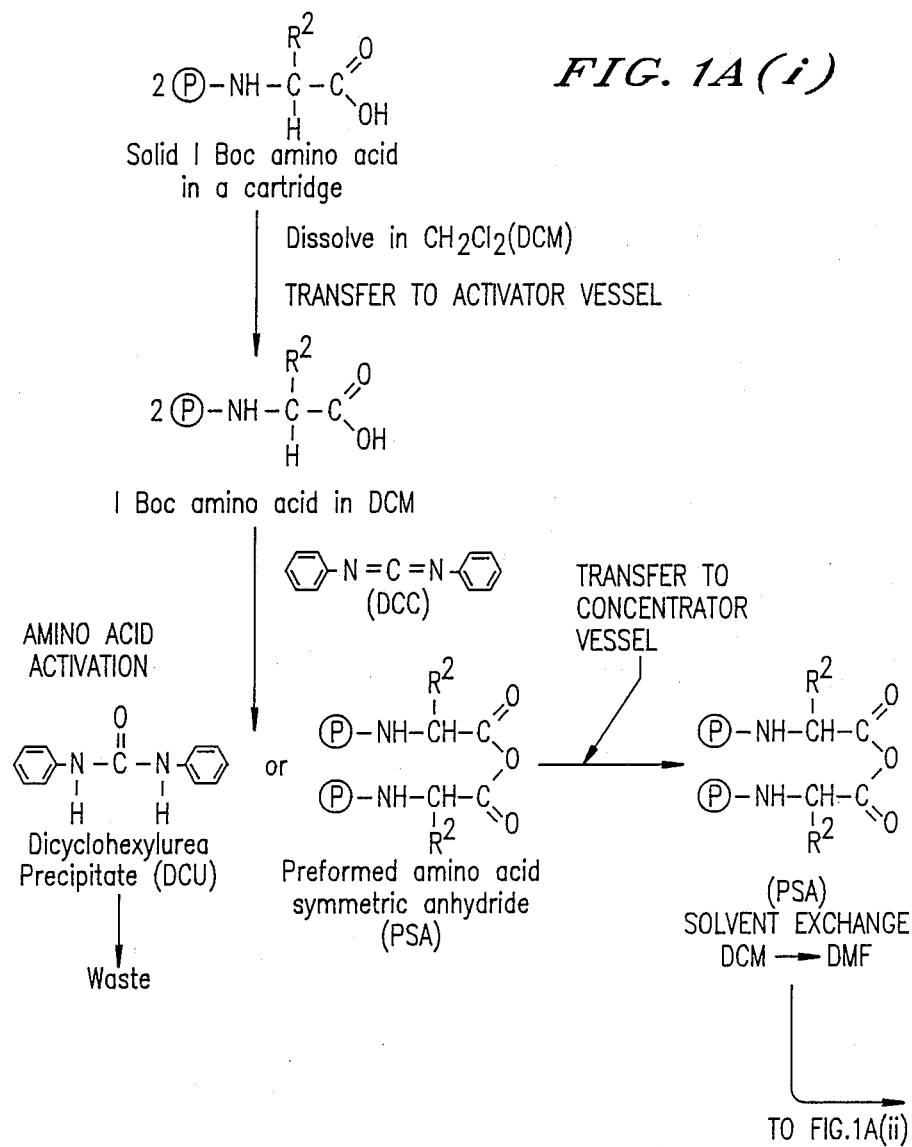
FIG. 1: Solid phase peptide synthesis applicable to preparing the present peptides and polypeptides.

Accordingly, it is an object of the present invention to provide new and improved materials for inhibiting mineral deposition.

It is another object of the present invention to provide materials for prevention of formation of calculus or plaque on teeth.

It is another object of the present invention to provide materials which can prevent mineralization in a marine environment, such as by prevention of barnacle accumulation.

It is yet another object of the present invention to provide materials which can effectively prevent mineralization on prosthetic devices implanted in the body.

It is yet another object of the present invention to provide materials for prevention of mineralization in arteries, associated with arteriosclerosis, or atherosclerosis.

It is yet another object of the present invention to provide for materials which can prevent mineralization in an industrial setting, such as scaling in water treatment plants.

It is yet another object of the present invention to provide for materials which can prevent corrosion of metallic surfaces.

It is yet another object of the present invention to provide for methods of prevention of the above-mentioned types of mineralization.

These and other objects of the present invention which will hereinafter become more readily apparent, have been accomplished by providing new polypeptide materials that are polyanionic on one end of the molecule and hydrophobic on the other end. These materials have the following general formula:

poly $(X)_n$ poly $(Y)_m$ where
each X independently is aspartic acid, glutamic acid, phosphoserine, phosphohomoserine, phosphotyrosine, or phosphothreonine,
each Y independently is alanine, leucine, isoleucine, valine, glycine or other nonpolar, amino acid residues,
n is 2 to 60,
m is 2 to 60, and
N+m is ≧5,
and wherein poly $(X)_n$ may contain up to 10% of the Y residues and poly $(Y)_m$ may contain up to 10% of the X residues, and salts thereof.

The present invention is also directed to compositions containing these materials, such as dentifrices and mouthwashes for oral application.

A more complete appreciation of the invention and many of the attendant advantages thereof, will be readily perceived as the same becomes better understood by reference to the following detailed description of preferred embodiments thereof.

DETAILED DESCRIPTION OF THE PREFERRED EMBODIMENTS

An interest in understanding better the chemical requirements for activity as inhibitors of mineralization prompted the inventors to identify new chemical structures of polypeptides that have surprisingly enhanced inhibitory activity. As a basis for this work, the inventors further elucidated the chemical structure of oyster shell proteins. They also took into consideration the structure of certain salivary proteins that inhibit crystallization (Hay, D. I. et al, Inorg. Persp. Biol. Med. 2, 271–285 (1979) and Calcif. Tiss. Int. 40, 125–132 (1987)).

The polypeptides of the present invention are synthetic polypeptides which possess clustered polyanionic amino acids at one end of the molecule and clustered non-ionic partly hydrophobic amino acids at the other end of the molecule. Preferably, the anionic amino acids are located at the C-terminus whereas the non-ionic amino acids are located at the N-terminus, although the opposite arrangement is also contemplated. Until the present invention, no one recognized that synthetic polypeptides having such a structure could be potent inhibitors of mineralization.

Although not wishing to be limited by a hypothesis as to the mechanism of action of the present polypeptides, the following is presented as a possible mechanism of action. The polyanionic region might stick to crystal surfaces, blocking growth there, while the hydrophobic region might extend from the surface and disrupt diffusion of lattice ions to other growth sites. This hypothesis is referred as the PH or polyanion/hydrophobe hypothesis. It is novel from the standpoint that crystal formation generally is thought to be limited not by diffusion but rather by the rate of surface reactions in which adsorbed ions become incorporated into crystal growth sites (Nancollas, G. H. and M. M. Reddy, J. Coll. Inter. Sci. 37, 824–830 (1971); Nancollas, G. H., Adv. Coll. Inter. Sci. 10, 215–252 (1979)). This conclusion is based on the calculated energy of activation of crystallization for CaCO$_3$ formation of 11.0 kcal/mole which is thought to be too high for a diffusion-controlled mechanism (Howard, J. R. et al, Trans. Faraday Soc. 56,278 (1960)), and on the observed lack of effect of the rate of stirring on rates of seeded crystal growth. Although this may be the case under some conditions, the inventors have often noticed that stirring is quite important and in fact must be carefully controlled to achieve reproducibility in many crystallization assays. They suggest that diffusion can be rate-limiting. In addition, studies of the effects of polyacrylates on the inhibition of crystallization suggested that low molecular weight polymers have the greatest effect on a weight basis (Rohm and Haas, op. cit.).

Based on the above information, the present inventors hypothesized that low molecular weight polypeptides (e.g. 500–5000 daltons) with a polyanionic/hydrophobic arrangement could have useful properties as inhibitors of mineralization.

Higher molecular weight polypeptides (e.g. 5000–10,000 daltons) having the clustered polyanionic/clustered hydrophobic structure of the above-described lower molecular weight polypeptides are also expected to have mineralization inhibitory activity and are therefore expected to have at least some of the same uses as the lower molecular weight polypeptides. However, the most active materials for the purposes of the present invention, on a weight basis, are the lower molecular weight polypeptides described herein.

The general structure of the polypeptides of the present invention is as follows:

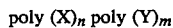

poly $(X)_n$ poly $(Y)_m$ where
each X independently is aspartic acid, glutamic acid, phosphoserine, phosphohomoserine, phosphotyrosine, or phosphothreonine,
each Y independently is alanine, leucine, isoleucine, valine, glycine or other nonpolar, amino acid residues,
n is 2 to 60, preferably 15-50, more preferably 30-50,
m is 2 to 60, preferably 3-15, more preferably 4-10,
n+m is ≧5, preferably n+m is 15-80, more preferably 15-40.
and salts thereof.

As can be seen from the general formula, the anionic amino acids are clustered on one end of the amino acid chain, whereas the nonpolar amino acids are clustered on the other end. Thus, these polypeptides are not random copolymers as disclosed by several of the prior art references discussed above. In the formula, the X amino acids may either be at the C-terminus or the N-terminus. In other words, the aspartic acid, glutamic acid, etc. residues may be segregated at the N-terminal or the C-terminal.

The X amino acids may be entirely comprised of any one of the X group, or may be any combination of members of the group. Similarly, the Y amino acids may be entirely any one of the Y group, or may be any combination of members of the group. For example, poly (X) could be made up entirely of phosphorylated amino acids.

Salts of any of the acidic residues set forth above, especially the sodium and potassium salts, are also within the scope of this invention. When phosphorylated amino acids are incorporated in the compounds, they may be present as salts, e.g., $Ca^{+2}$, $Mg^{+2}$, di-$Na^+$, di-$K^+$, and the like. Further, salts of the amino group, such as the p-toluenesulfonate, acetate, etc. are also contemplated.

Peptides wherein up to 10% of the X (anionic) residues are replaced by Y (non-polar) residues and vice versa are also within the scope of this invention. To illustrate this possibility, the following peptide is considered:

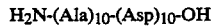
$H_2N-(Ala)_{10}-(Asp)_{10}-OH$

The Y residues are ten alanines. One of these residues (10%) could be replaced by an anionic residue (e.g., aspartic acid or glutamic acid). Similarly, the X residues are ten aspartic acid residues. One of these could be replaced by a non-polar amino acid (e.g., alanine, glycine, valine, etc.). Naturally, only integral numbers of replacement amino acids are possible.

Specific preferred examples of formulas of polypeptides according to the present invention are the following:

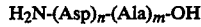
$H_2N-(Asp)_n-(Ala)_m-OH$

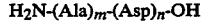
$H_2N-(Ala)_m-(Asp)_n-OH$

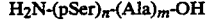
$H_2N-(pSer)_n-(Ala)_m-OH$

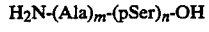
$H_2N-(Ala)_m-(pSer)_n-OH$

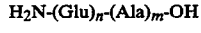
$H_2N-(Glu)_n-(Ala)_m-OH$

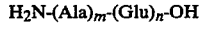
$H_2N-(Ala)_m-(Glu)_n-OH$

$H_2N-(Ala)_m-(Asp)_n-(pSer)_x-OH$

$H_2N-(Ala)_m-(Glu)_n-(pSer)_x-OH$ wherein
n=10-60, preferably 15-50.
m=2-10, preferably 3-8.
x=2-5, preferably 2-3.
[pSer=p ne; that is, serine which has been phosphorylated on the side chain hydroxyl].

In each of the above formulas, some or all of the alanine residues may be replaced by other nonpolar amino acids, such as leucine, isoleucine, valine and glycine. Similarly, some or all of the aspartic acid residues may be replaced by other anionic amino acids such as glutamic acid, and vice versa. Further, some of the glutamic acid residues or aspartic acid residues may be replaced by phosphoserine, phosphohomoserine, phosphotyrosine, phosphothreonine or other phosphorylated amino acids. Generally, amino acids containing a free hydroxyl group can be phosphorylated on the hydroxyl group. The phosphoserines could also be phosphohomoserine, phosphotyrosine, or phosphothreonine.

Some specific preferred embodiments of the present invention are the following compounds:

$H_2N-(Ala)_5-(Asp)_{18}-(pSer)_2-OH$

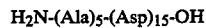
$H_2N-(Ala)_5-(Asp)_{15}-OH$

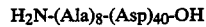
$H_2N-(Ala)_8-(Asp)_{40}-OH$

As can be seen from the above description of the present compounds, a large number of polypeptides fall within the scope of the present invention. However, each of them has in common the structural feature of clustered hydrophobic or nonpolar amino acids on one end of the polypeptide and clustered anionic amino acids on the other end of the polypeptide. They are also generally small polypeptides having from 10-80 amino acid residues, preferably 10-60 amino acid residues, most preferably 20-50 amino acid residues.

METHODS OF SYNTHESIS

The products of the invention may be synthesized by any number of techniques now available for synthesis of simple and complex low molecular weight polypeptides. Generally speaking, these techniques involve stepwise synthesis by successive additions of amino acids to produce progressively larger molecules. The amino acids are linked together by condensation between the carboxyl group of one amino acid and the amino group of another amino acid to form a peptide bond. To control these reactions, it is necessary to block the amino group of one amino acid and the carboxyl group of the other. The blocking groups should be selected for easy removal without adversely affecting the polypeptides, either by racemization or by hydrolysis of formed peptide bonds. Certain amino acids have additional functional groups such as the carboxyl groups of aspartic acid and glutamic acid and the hydroxyl groups of serine, homoserine and tyrosine. It is usually necessary to block these additional groups with an easily removed blocking agent, so that they do not interfere with the desired condensation for the formation of peptide bonds.

A wide variety of procedures exist for the synthesis of polypeptides, and a wide variety of blocking agents have also been devised. Most of these procedures are applicable to the peptides of the present invention. The preferred method for synthesis of the subject peptides is a solid-phase technique. In this procedure, an amino acid is bound to a resin particle, and the peptide is generated in a stepwise manner by successive additions of protected amino acids to the growing chain. The general procedure is well known, and has been described in many articles, for example: Merrifield, R. B., J. Am. Chem. Soc. 96, 2986–2993, 1964.

A preferred solid-phase method is described hereinbelow.

The peptides were made using automated, solid-phase peptide synthesis as depicted in FIG. 1. The carboxy terminal amino acid was preloaded via an organic linker (PAM, 4-oxymethyl phenylacetamidomethyl) covalently attached to an insoluble polystyrene resin cross-linked with divinyl benzene.

In this preferred embodiment, the C-terminus of the polypeptides was aspartate and the C-terminal region polyanionic, with hydrophobic residues added to the PH polypeptides on the N-terminus. This is the opposite of the structure of related natural protein inhibitors. The reason for this orientation is that the aspartate-PAM linkage is easier to cleave at the end of the synthesis as compared to hydrophobic amino acid-PAM linkages, resulting in greater yields. It is not likely that the positioning of the polyanionic or hydrophobic regions at the C vs. the N terminus matters with regard to activity.

The t-Boc strategy of protection of the terminal amine was used. The side chain carboxyl group of aspartate and the OH of serine were both protected by O-benzyl groups. Final cleavage of the peptide from the resin and final R-group deprotection was achieved using hydrofluoric acid (HF) or trifluoromethyl sulfonic acid (TFMSA) according to established procedures (Bergot, B. J. and S. N. McCurdy, Applied Biosystems Bulletin (1987)). An automated peptide synthesizer (Applied Biosystems, model 430-A) was used. A routine synthesis produced 0.5 mmole of peptide-resin. Yield after cleavage and purification was approximately 60 to 70%.

Purification was accomplished by recrystallizing the peptides from an organic solvent such as methyl-butyl ether, then dissolving the crystals in a small amount (e.g. 5.0 ml) of distilled water in a dialysis bag (MW cutoff 500 daltons), dialysis for removal of residual solvents, and lyophilization. Purity of the peptides was checked by reversed-phase liquid chromatography (Varian 5560) using a C-18 column and 0.1% trifluoroacetic acid and acetonitrile as solvents, or by gel permeation using a column for separations between 1000 and 30,000 daltons with 0.05M trishydroxymethyl amino methane (pH 8.0) as the mobile phase. This approach yielded peptides of precisely-known sequence and molecular size.

Alternatively, polyanionic/hydrophobic peptides of approximately-known sequence and size may be made by conventional thermal polymerization of the polyanionic region and the hydrophobic regions separately using R-group protected amino acids (Melius, P. and J. Y. P. Sheng, Bioorg. Chem 4, 385 (1975)). Next the polyanionic and hydrophobic regions can be linked thermally, followed by deprotection of the R-groups using cleavage reagents There is some evidence to suggest that a polyanionic/hydrophobic peptide may assemble naturally under thermal polymerization conditions, without the need for separate synthesis followed by attachment of the two regions (Phillips, R. D. and P. Melius, Int. J. Peptide Protein Res. 6, 309–319 (1974)).

A preferred embodiment of the peptide inhibitors involves the incorporation of 2 or more phosphoserine residues at any location in the polyanionic region of the molecule. This idea is consistent with the known activity of simple phosphate and polyphosphates as inhibitors of crystallization and the similar activity of phosphonates. In addition, the inventors' work and recent reports (Hay, D. I. et al, Calcif. Tissue Int. 40, 126–132 (1987)) suggest that the presence of phosphoserine residues in natural proteins significantly enhances inhibitory activity. Therefore, peptides containing phosphoserine have been prepared according to the method of Riley et al., J. Am. Chem. Soc. 1957, 1373–1379.

This method involves derivitization of serine residues after peptide synthesis using diphenyl phosphochloridate in the ratio of X moles serine to X+1 moles of the phosphochloridate at room temperature for 2 hours with dimethylformamide as solvent. This produces a diphenyl phosphate ester plus polypeptide that can be recrystallized from ether. The phosphopeptide ester is then dissolved in 0.1M $NH_4HCO_3$ and the phenyl groups removed by reduction by sparging with $H_2$ gas in the presence of a platinum or palladium oxide catalyst. The phosphopeptide is then recrystallized and purified. Other useful derivatives, for example, sulfated, phosphonated, and sulfonated peptides are also contemplated. In each case, a phosphate moiety could be replaced with a sulfate, phosphonate or sulfonate group.

ACTIVITY ASSAYS

To measure the ability of the peptides of the present invention to inhibit mineralization, a number of assays have been developed. These assays include the following:

1. pH-drift assay-$CaCO_3$.
2. pH-drift assay calcium phosphate.
3. pH-stat assay-$CaCO_3$.
4. constant composition assay-$CaCO_3$.

The following examples describe how these various assays have been employed to measure the ability of the polypeptides to inhibit mineralization.

EXAMPLE 1

The pH-drift assay-Calcium Carbonate

A solution supersaturated with respect to $CaCO_3$ is prepared by separately pipetting 0.3 ml of 1.0M $CaCl_2$ dihydrate and 0.6 ml of 0.5M $NaHCO_3$ into 29.1 ml of artificial seawater (0.5 NaCl, 0.011M KCl). The reaction vessel is a 50 ml, 3-necked, round-bottom flask partially immersed in a thermostated water bath at 20° C. The reaction vessel is closed to the atmosphere to minimize exchange of $CO_2$. The reaction is started by adjusting the pH upward to 8.3 by titration of $\mu l$ amounts of 1N NaOH by digital pipette. The initial concentrations are 10 mM each of $Ca^{2+}$ and dissolved inorganic carbon (DIC). The reaction is monitored by pH electrode and recorded by strip chart.

Figure 2:
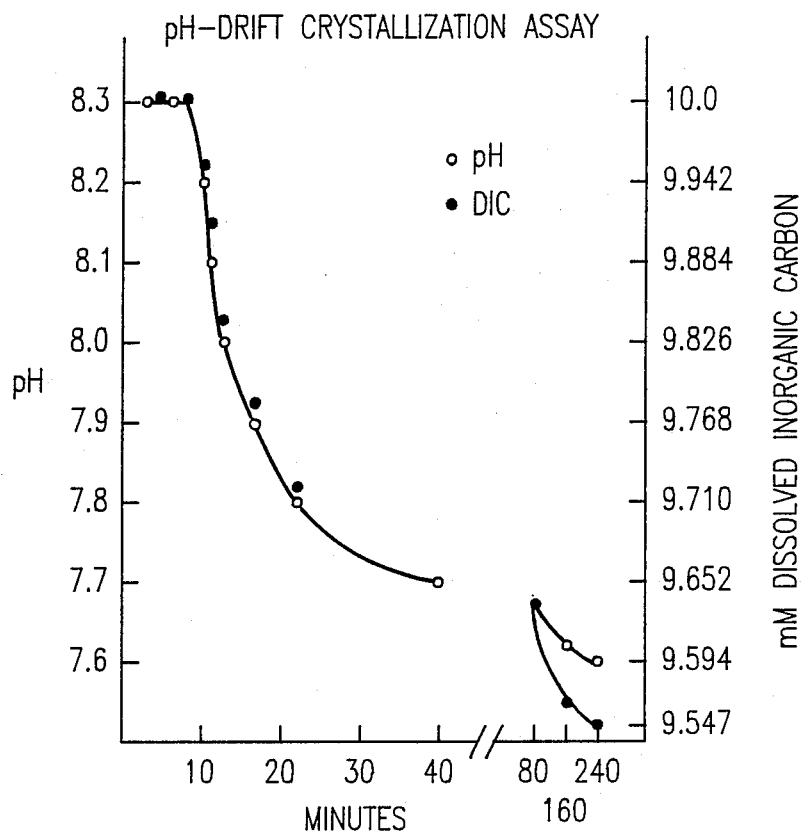
FIG. 2: Data obtained from a pH-drift crystallization assay.

After a period of stable pH during which crystal nuclei form, the pH begins to drift downward until the reaction ceases due to depletion of reactants and the lowering of pH. The reaction may be quantified by calculations based on DIC equilibria to give the amount of precipitation versus time. In FIG. 2 it can be seen that a change in pH is directly proportional to a change in DIC from pH 8.3 to 7.7, but below 7.7 the buffering effect of the DIC system leads to greater changes in DIC per unit pH.

EXAMPLE 2

The pH-drift assay: Calcium Phosphate

A solution supersaturated with respect to calcium phosphate is prepared by separately pipetting 0.1 ml of 1.32M $CaCl_2$ dihydrate and 0.1 ml of 0.90M $NaH_2PO_4$ into 29.8 ml of distilled water. This yields initial concentrations of 4.4 mM $Ca^{2+}$ and 3.0 mM dissolved inorganic phosphorus (DIP). The reaction vessel is a 50 ml, round-bottom, 3-necked flask partially immersed in a thermostated water bath at 20° C. The reaction vessel is closed to the atmosphere. The reaction begins upon mixing the reactants with an initial pH of 7.4.

FIG. 3 shows data obtained from this type of assay. Amorphous calcium phosphate (ACP) nucleates immediately and slowly grows as indicated by a slight decrease in pH during the first 30 minutes or so of the assay. Following this, ACP begins to transform to calcium hydroxylapatite (HAP), $Ca_{10}(PO_4)_6(OH)_2$, as indicated by a marked acceleration in the downward pH drift. The reaction ceases as reactants are depleted and the pH is lowered.

EXAMPLE 3

The pH-stat assay

Figure 4A:
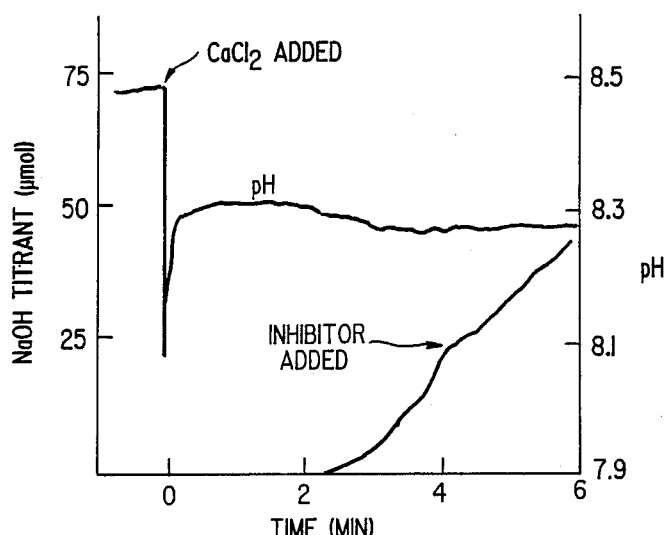
FIG. 4: Graphs showing the initial growth rate of $CaCO_3$ crystals (A), the growth rate of crystals after matrix addition (b), and crystal growth rate (C) after the addition of an inhibitor as determined in a pH-stat.
Figure 4B:
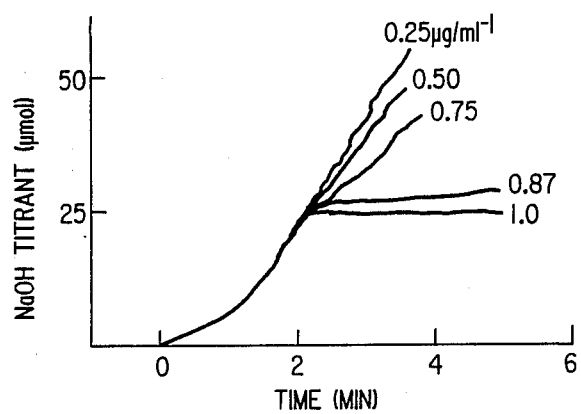
Figure 4C:
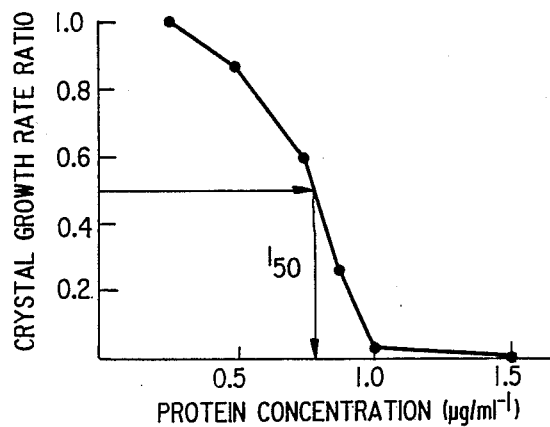

The following description relates to FIG. 4.

A. The effect on $CaCO_3$ crystallization of various concentrations of EDTA-extracted soluble matrix from oyster shell were compared in the pH-stat assay. The medium consisted of 25 ml 0.5M NaCl, 0.01M KCl, and 10 mM DIC with the initial pH adjusted to 8.5. The reaction vessel was thermostated at 25° C. To initiate crystal growth, $CaCl_2$ was added to a final concentration of 10 mM (first arrows). After an initial decrease in pH to 8.3, probably due to ion-pairing, and an induction period of approximately 2 minutes, crystals appeared in solution.

The crystal growth is proportional to the amount of 0.5M NaOH titrant required to maintain a constant pH during the overall reaction $Ca^{2+} + HCO_3^- \rightarrow CaCO_3 + H^+$. The pH was held constant by autotitration.

B. After crystals grew to an equivalent of 25 μmol of titrant, various quantities of matrix were added (second arrow) ranging from 0.5 μg/ml (a) to 1.5 μg/ml (d) final concentration. Note that the rate of crystal growth after addition of matrix decreased relative to the control rate as matrix concentration increased, and growth was terminated at 1.5 μg/ml.

C. For comparing various inhibitors (for example, see Table 1), the growth rate immediately following the addition of inhibitor is calculated as a percent of the growth rate of the crystals before the addition of inhibitor. From examining the effects of a series of concentrations, the quantity of inhibitor required to reduce the control rate of crystal growth by 50% can be determined graphically.

EXAMPLE 4

The Constant Composition Assay: The Effect of Oyster Shell Matrix, Polyaspartate, and HEDP on the rate of $CaCO_3$ crystal growth A 50 ml solution of 10 mM $CaCl_2$ and 10 mM dissolved inorganic carbon (DIC) was adjusted to pH 8.34 by digital pipetting of μl amounts of 1N NaOH. The temperature was held constant at 20° C. using a water-jacketed reaction vessel and a thermostated bath. After about a 6 minute period during which $CaCO_3$ nucleation occurs, the pH begins to drift downward as $Ca^{2+}$ and $CO_3^{2-}$ ions are removed from solution as solid crystals. At pH 8.30, inhibitors were added which stabilized the pH drift for certain periods of time. The concentrations of inhibitors used in the experiments shown in FIG. 5 were matched so that the amount of stabilization or inhibition of nucleation was the same, in this case about 2 hours. The doses required for this effect ranged between 0.1 to 0.5 μg/ml of inhibitor depending on the type. When crystallization began again, the pH would drift downward. However, it was held constant at pH 8.30±0.02 by automatic titration of 0.5M $CaCl_2$ and 0.5M $NaCO_3$ from separate burettes linked via the pH electrode to a computer-assisted titrimeter.

Figure 5:
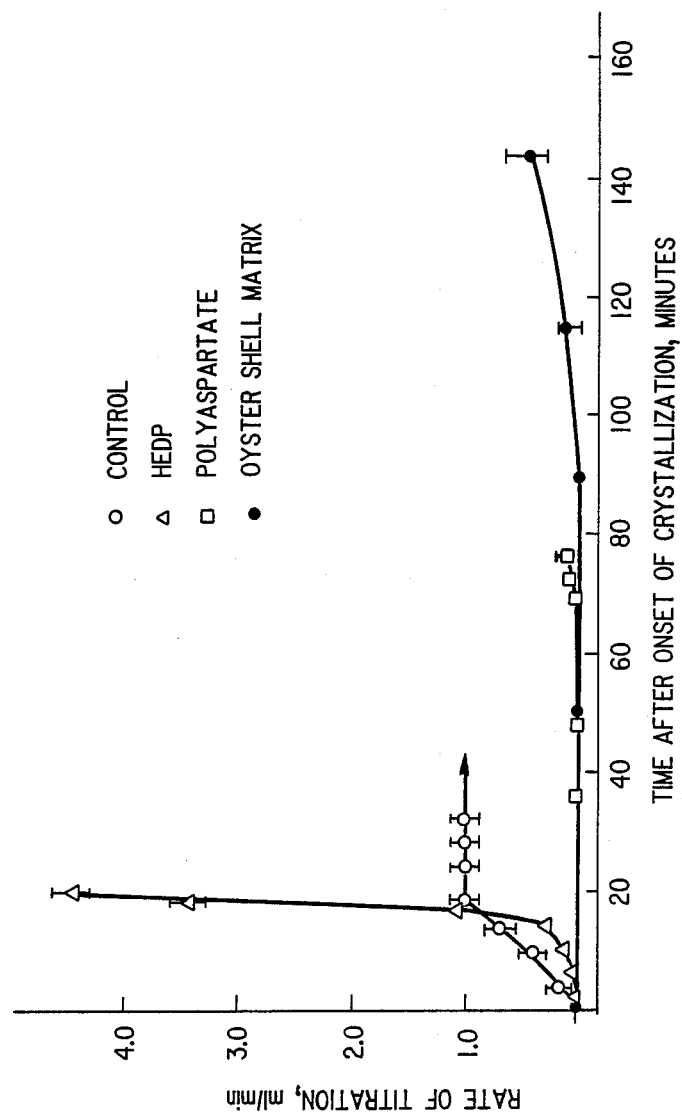
FIG. 5: Data obtained from a $CaCO_3$ crystallization, constant composition assay.

In FIG. 5, notice the dramatic acceleration of the rate of crystallization in the presence of hydroxyethylidene diphosphonate (HEDP), perhaps the most commonly-used $CaCO_3$ inhibitor for water treatment. This effect was not observed in the presence of matrix or the matrix analog over the time periods studied. These results suggest quite different mechanisms of action for the two classes of crystallization inhibitors.

EXAMPLE 5

The effects of synthetic peptides on $CaCO_3$ crystallization

Figure 6:
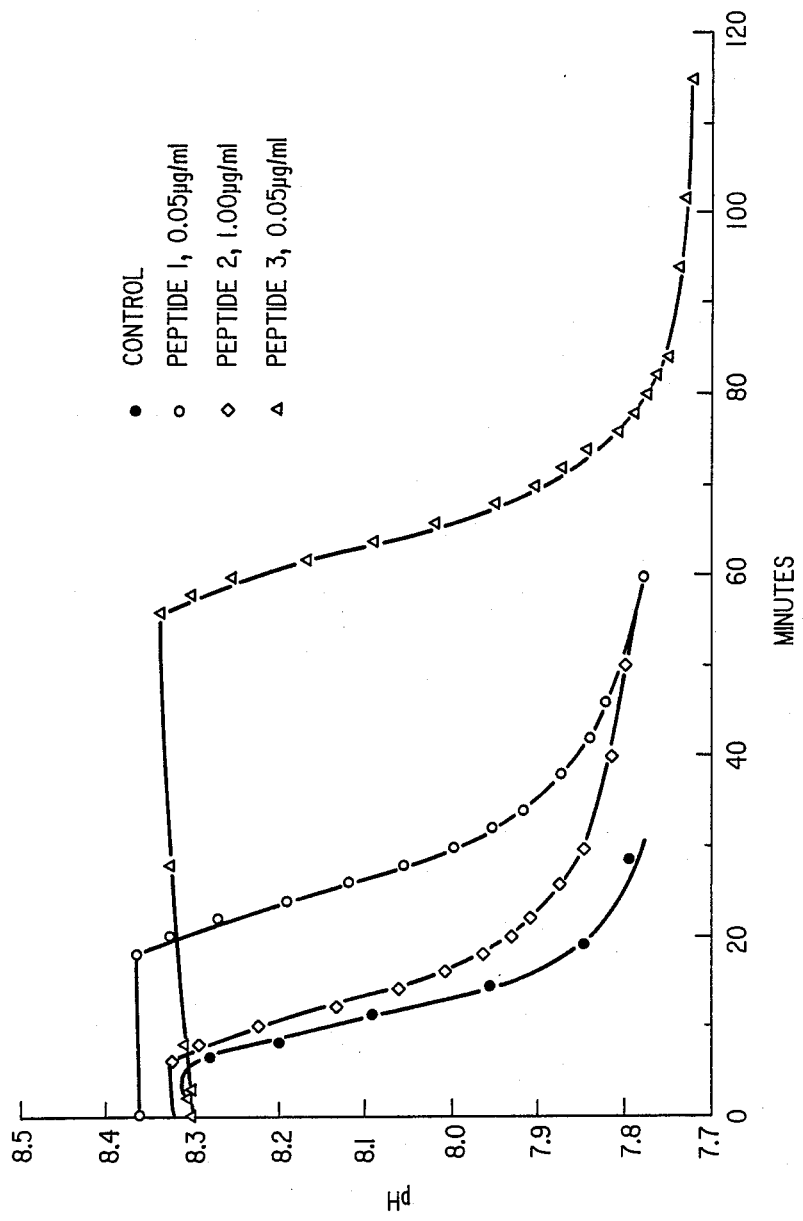
FIG. 6: The effects of synthetic peptides on $CaCO_3$ crystallization ($CaCO_3$ pH-drift assay).

The calcium carbonate pH-drift assay was used to assay three peptides, peptides 1, 2 and 3. Peptide 1=poly (Asp)$_{20}$, peptide 2=poly (Asp-Gly)$_7$ (Ala)$_6$, and peptide 3=poly (Asp)$_{15}$ (Ala)5. The conditions of the assay were 10 ml Ca, 10 ml dissolved inorganic carbon at 20° C. and 30 ml of artificial seawater (0.5M NaCl, 0.01M KCl). The results are shown in FIG. 6.

Peptide 3, a PH peptide, exhibited significantly enhanced inhibition of crystal nucleation, the formation of new crystals in solution. The effect on nucleation is seen in the increased duration of the induction period of stable pH prior to the period of crystal growth when pH drifts downward. No effect on crystal growth (the increase in size of pre-existing crystals) was observed in this assay, as shown by the slope of the recorder tracing during the phase of crystal growth. The activity of the PH peptide was compared to that of a polyaspartate of equivalent chain length (peptide 1) at equal doses. It was also interesting to note that an ordered copolymer of aspartate-glycine with a hydrophobic tail of alanine residues (peptide 2) has very little activity relative to the control curve. The repeating Asp-Gly arrangement is the structure predicted for acidic proteins from mollusc shells based on published reports (e.g., Weiner, S., Biochemistry 22, 4139–4145 (1983))

EXAMPLE 6

Inhibition of $CaCO_3$ crystallization by synthetic peptides: pH-drift assay A more detailed comparison of effects as seen in Example 5 is presented in Table 1. The PH peptide H-(Ala)$_5$-(Asp)$_{15}$-OH exhibited the greatest inhibition of crystal nucleation. Again, there was no clear effect on crystal growth using this assay. The relative lengths of the polyanionic and hydrophobic regions are important to inhibitory activity as shown by decreased activity of the PH peptide H-(Ala)$_{10}$-(Asp)$_{10}$-OH.

The length of the polyanionic region that provides the greatest affinity for crystal surfaces falls in the range of (Asp or Glu)$_{15}$ to (Asp or Glu)$_{60}$, with preferred lengths in the range (Asp or Glu)$_{30}$ to (Asp or Glu)$_{50}$. The preferred length of the hydrophobic region falls in the range of 3 to 8, e.g. (Ala)$_3$ to (Ala)$_8$.

Peptides that might have been predicted to have high activity (the last 4 peptides) based on published reports about the structure of natural inhibitory proteins did not exhibit enhanced activity relative to the performance of polyaspartate or the more active PH peptide. These last 4 peptides are ordered copolymers of aspartate, glycine, and serine, in one case having a polyalanine tail.

induction period. But the pH-drift assay is not good for measuring crystal growth because the reaction is self-limiting during crystallization due to depletion of reactants and lowering of pH.

In these experiments, all of the polypeptides were added to the medium of crystal growth at a dose of 0.02 $\mu$g/ml prior to the addition of 2.5 mg of CaCO$_3$ seeds. The specific effect of increased inhibition of crystal growth was seen as the length of the polyalanine tail was increased to 10 residues with the polyaspartate region kept at 15 residues. For comparative purposes, polyaspartate molecules of increasing chain lengths were also tested.

TABLE 1

INHIBITION OF CaCO$_3$ CRYSTALLIZATION BY SYNTHETIC PEPTIDES pH-DRIFT ASSAY

| PEPTIDE | CONCENTRATION $\mu$g/ml | INDUCTION PERIOD, MIN | CRYSTAL GROWTH RATE, pH/MIN |
|---|---|---|---|
| CONTROL | — | 7.1 ± 1.96 | 0.048 ± 0.0041 |
| H—(ASP)$_{20}$—OH | 0.02 | 21.5 ± 0.50 | 0.047 ± 0.0030 |
| (polyaspartate) | 0.035 | 39.2 ± 10.8 | 0.041 +0.0050 |
|  | 0.050 | >180 | — |
| H—(ALA)$_5$-(ASP)$_{15}$—OH | 0.005 | 11.3 ± 3.37 | 0.047 ± 0.0025 |
|  | 0.01 | 35.4 ± 13.8 | 0.040 ± 0.0034 |
|  | 0.02 | >180 | — |
| H—(ALA)$_{10}$(ASP)$_{15}$—OH | 0.050 | 32.0 ± 10.4 | 0.042 ± 0.0039 |
| H—(GLY-ASP)$_{10}$—OH | 0.10 | 36.0 ± 5.20 | 0.047 ± 0.0097 |
| H—(ALA)$_6$-(GLY-ASP)$_7$—OH | 0.20 | 7.2 ± 0.83 | 0.048 ± 0.0042 |
| H—(SER-ASP)$_{10}$—OH | 0.1 | 29.8 ± 4.99 | 0.048 ± 0.0040 |
| H—(GLY-SER-ASP)$_7$—OH | 0.1 | 5.83 ± 1.04 | 0.057 ± 0.0034 |

EXAMPLE 7

Figure 7:
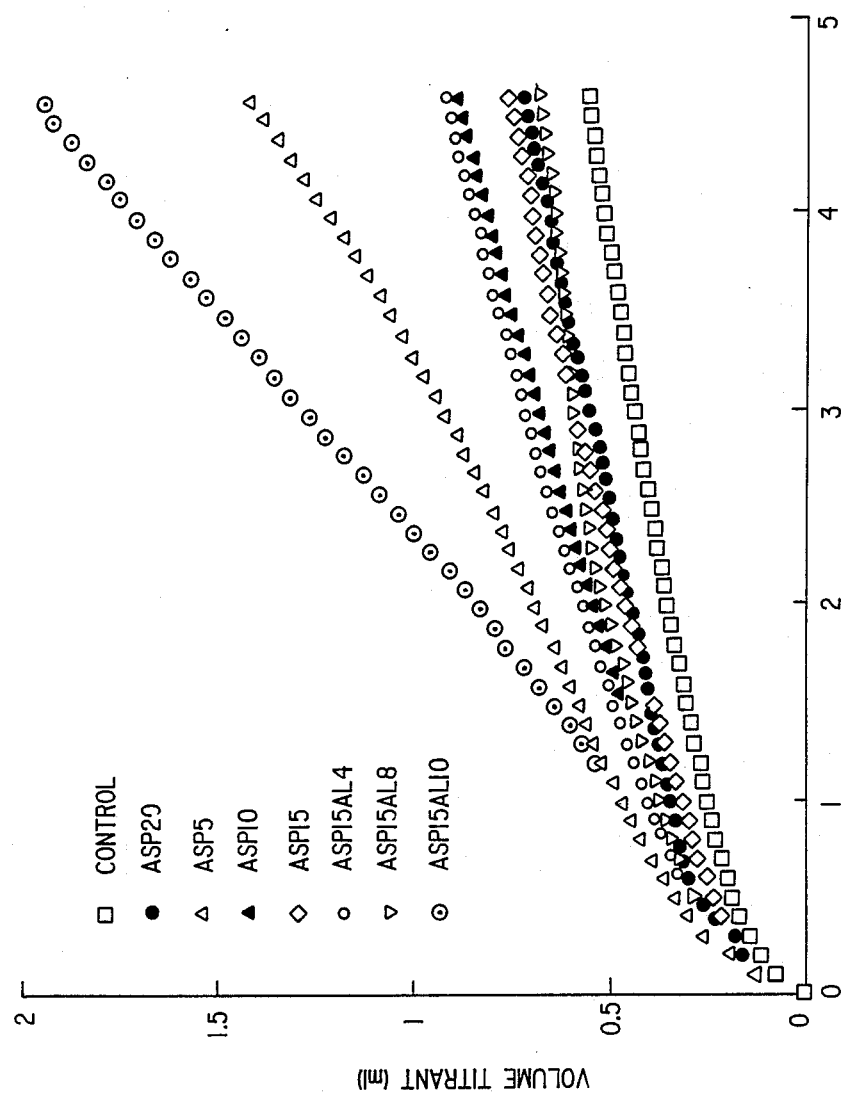
FIG. 7: Inhibition of CaCO$_3$ crystal growth by synthetic peptides; constant composition seeded crystal assay.

Inhibition of CaCO$_3$ crystal growth by synthetic peptides: constant composition/seeded crystal assays In this assay, 0.1 ml of 10M CaCl$_2$ and 0.2 ml of 0.5M NaHCO$_3$ are added to 49.7 ml of artificial seawater. To start the reaction, 0.1 ml of an aqueous slurry of CaCO$_3$ crystals (Baker Analytical Reagents) is added, and the pH is adjusted to 8.5 by titration of $\mu$liter amounts of 1N NaOH. Crystals begin to grow immediately in the solution, which is 2.0 mM Ca$^{2+}$ and 1.6 mM dissolved inorganic carbon. The reaction again is monitored by a pH electrode linked to a computer assisted titrator set to maintain the pH at 8.50. The titrator simultaneously adds 0.1M CaCl$_2$ and 0.1M Na$_2$CO$_3$ (pH 11.0) to replace the Ca$^{2+}$ and CO$_3^{2-}$ that are removed from solution as CaCO$_3$ crystals grow. Thus, the chemical potential of the solution is kept constant. When inhibitors are used, they are added after the addition of the calcium. The experiments shown in FIG. 7 represent average results for at least triplicate assays for each molecule. Control curves are run before or after each set of experimental curves. This assay reveals clearer effects of inhibitors on crystal growth because growth can be monitored under constant conditions over extended periods. Effects of inhibitors on crystal nucleation, on the other hand, are not seen in this assay because there is no induction period prior to crystal growth during which nucleation occurs. Conversely, the pH-drift assay is best for measuring effects on nucleation as shown by changes in the induction period. But the pH-drift assay is not good for The results suggest that the most active molecules on a weight basis will have a specific chain length of the polyanionic region to provide optimum affinity for crystal surfaces. In addition, a specific chain length of the hydrophobic region is required, presumably to provide optimum coverage of the crystal surface including the zone immediately surrounding the surface.

EXAMPLE 8

The effect of some inhibitors on calcium phosphate formation

The data in Table 2 show that CaCO$_3$ crystallization inhibitory activity of a molecule can also be applied to calcium phosphate formation. Both the oyster shell protein and polyaspartate can inhibit both CaCO$_3$ and calcium phosphate formation. The presence of phosphorylated residues in the oyster shell protein enhances the inhibitory activity with respect to amorphous calcium phosphate (ACP) formation and apatite formation.

The effects of some other molecules are shown for comparative purposes. The phosphino-carboxylate copolymer and polymaleate are representative of industrial polymers currently in use for prevention of mineral scaling in cooling towers and other equipment. The phosphonate diethylene triamine pentamethylene phosphonic acid (DENTPP), is the most effective phosphonate known for inhibition of calcium phosphate formation. The salivary protein statherin is the most effective inhibitor among a group of salivary proteins that regulate mineral deposition in the oral cavity.

TABLE 2

EFFECT OF SOME INHIBITORS ON CALCIUM PHOSPHATE FORMATION[1]

| INHIBITOR | PERIOD OF ACP FORMATION | pH/min, ACP FORMATION | pH/min, APATITE FORMATION |
|---|---|---|---|
| None (control, n = 20 ± S.D.) | 31.3 ± 4.36 min | 0.0047 ± 0.0023 | 0.090 ± 0.013 |
| Oyster shell matrix, phosphor- | 65 minutes | 0.0030 | 0.068 |

TABLE 2-continued
EFFECT OF SOME INHIBITORS ON CALCIUM PHOSPHATE FORMATION[1]

| INHIBITOR | PERIOD OF ACP FORMATION | pH/min, ACP FORMATION | pH/min, APATITE FORMATION |
|---|---|---|---|
| ylated, 10 µg/ml[2] | | | |
| Oyster shell matrix dephosphorylated, 10 µg/ml | 40 minutes | 0.0034 | 0.105 |
| Polyaspartate, MW 15,000, 10 µg/ml | 30 minutes | 0.0040 | 0.106 |
| Polyaspartate, MW 15,000, 15 µg/ml | 48 minutes | 0.0050 | 0.070 |
| Phosphino-carboxylate copolymer, 10 µg/ml | 69 minutes | 0.0025 | 0.052 |
| Polymaleate, 10 µg/ml | 83 minutes | 0.0014 | 0.051 |
| DENTPP, phosphonate, 5 µg/ml | 100 minutes | 0.0012 | 0.019 |
| Statherin[3] 37 µg/ml | 48 minutes | 0.0045 | 0.0090 |

[1]Assay Conditions: Ca at 4.4 mM, dissolved inorganic phosphorus at 3.0 mM, initial pH 7.40, 20° C.
[2]Results for experimental molecules are given as the average values for at least triplicate experiments.
[3]Adapted from Hay, D.I., E.L. Moreno, and D. H. Schlesinger. 1979. Phosphoprotein-inhibitors of calcium phosphate precipitation from salivary secretions. Inorganic Perspectives in Biology and Medicine 2, 271-285.

EXAMPLE 9
The effect of phosphorylation on inhibition of $CaCO_3$ formation by oyster shell matrix The purpose of the measurements reported in Table 3 was to clarify the influence of phosphorylation of the oyster shell protein on its activity with respect to $CaCO_3$ formation. Again, it is clear that the presence of phosphorylated residues leads to significantly enhanced inhibitory activity.

TABLE 3
EFFECT OF PHOSPHORYLATION ON INHIBITION OF $CaCO_3$ FORMATION[1] BY OYSTER SHELL MATRIX[2]

| | Pi % by wt. | $I_{50}$ µg ml$^{-1}$ |
|---|---|---|
| Untreated | 13.6-15.8 (N = 8) | 1.4-2.2 (N = 8) |
| Partial dephosphorylated[3] | 7.2-10.0 (N = 3) | 2.5-3.4 (N = 3) |
| Dephosphorylated | 0.6-3.7 (N = 4) | 6.4-8.3 (N = 3) |

[1]Assay conditions: 10 mM Ca, 10 mM dissolved inorganic carbon, 25 ml artificial seawater, pH 8.3, pH-stat assay.
[2]The protein from oyster shell was solubilized by dissolution of crushed shell in 10% EDTA, pH 8.0, followed by isolation using gel permeation (sephacryl) to yield a fraction of about 30,000 daltons that was then concentrated by tangential flow dialysis, lyophilized, and frozen.
[3]Dephosphorylation was accomplished by treatment with alkaline phosphatase according to Termine, J. D. and K. M. Conn, 1976, Inhibition of apatite formation by phosphorylated metabolites and macromolecules, Calcif. Tiss. Res. 22, 149-157. Phosphorus was measured spectrophotometrically according to Marsh, B. B., 1959, The estimation of inorganic phosphate in the presence of adenosine triphosphate. Biochem. Biophys. Acta 32, 351-361.

Uses of the Present Polypeptides

The various polypeptides of this invention may be utilized directly without additives or carriers for inhibiting the deposition of minerals such as phosphates and carbonates whether of inorganic or biological origin. Uses for inhibition of other salts of carbonate, phosphate and sulfate, e.g., magnesium or barium salts, are contemplated. The various polypeptides may be utilized by adding an effective amount of the inhibitor to a liquid in contact with a surface on which the deposits may form. Such is the case of industrially useful and commercially important containers, i.e., boilers, piping, desalinators, cooling towers, and the like. The various amino acid polymers of this invention can be added to water, water-containing liquids or other liquids in an amount as small as 0.01 ng/ml. The upper limit for the amount of the inhibitor is generally only given by its solubility in the liquid to which it is added. However, if the presence of insoluble residues of these polymers does not interfere with industrial operations, it may be desirable to add these inhibitors in an amount greater than that given by their solubility limit. A preferred range of the various peptide derivatives for controlling inorganic scaling of e.g., calcium carbonate is $10^{-4}$–$10^2$ µg/ml. Other preferred ranges are $10^{-4}$–$0.1$ µg/ml and $0.1$–$10^2$ µg/ml of the various polymeric derivatives.

When the present inhibitors are utilized for their antifouling characteristics in order to prevent the encrustrations of plant or animal organisms, they can be added to a liquid such as water, water-containing liquids or other non-aqueous liquids, preferably in an amount about 0.001–1,000 µg/ml, although larger amounts can also be used. Used within this range of concentrations, the present inhibitors find an application in the prevention of encrustration of organisms in, e.g., running water piping or sewage piping, among others.

The present inhibitors can also be applied directly to a surface before it comes in contact with mineral containing liquids, e.g., industrial containers, marine surfaces such as those in piers, ships, and the like. The present inhibitors may be applied by themselves or in combination with other salt deposition inhibitors, antirust agents, or the like and/or with a carrier, directly to the exposed surface, or they may be mixed with other polymers used for the protection of said surfaces. A variety of carriers are contemplated for the application of the present inhibitors. Some of the most common carriers include aqueous and non-aqueous liquids, gels, oils, organic and inorganic solvents, compressed gases, and the like. However, any carrier may be used according to the needs. When used in high concentrations by themselves, the poly amino acid inhibitors of this invention may be highly viscous and can be easily applied to a surface. After the application of the inhibitors, an appropriate length of time may be allowed for the penetration of the inhibitor into the surface, as is the case with porous surface materials, such as wood, ceramics and the like. Thus, a large storage of the present inhibitors is created within the material and the surface may then be partially sealed with a coat-forming polymer to retard release of the active component. Alternatively, the various polypeptides may be mixed with a carrier to form a suspension which can be applied to a surface. The present inhibitors may be applied to any type of surface which may be exposed to the formation of inorganic or biological mineral deposits. Some of the most common materials to which the present inhibitors may be applied are metals, woods, synthetic polymers and copolymers, glass, ceramics, and painted or otherwise coated surfaces, although other materials are also contemplated. When in contact with the mineral-containing liquid, the inhibitors will slowly leach out from underneath the polymeric coating layer. The present inhibitors may further be applied in admixture with the coating forming polymer, e.g., paints or any synthetic polymer used for the protection of surfaces such as polyurethanes. When the present inhibitors are used in admixture with a coat-forming polymer, they can be used in a concentration of between 0.001–90% by weight of the total composition, although higher or lower concentrations are also contemplated in this invention. Some of the preferred concentrations are 1–75% by weight. Other preferred concentrations are 5–25%, 25–50% and 10–40% by weight. When applied to a surface the present inhibitors may be formulated with a carrier in the form of powder, solution, suspension, gel, oil, aerosol, paste or viscous colloid.

In a preferred embodiment of the present invention, the present materials may serve as inhibitors of dental tartar and plaque formation (referred to herein as tartar barrier agents) for human or animal use. In accordance with this embodiment of the present invention, the oral compositions may comprise any conventional pharmaceutically acceptable oral hygiene formulation that contains and is compatible with an effective amount of an antidental calculus agent as disclosed herein. Such formulations include, for example, mouthwashes, rinses, irrigating solutions, abrasive and non-abrasive gel dentifrices, denture cleansers, coated dental floss and interdental stimulator coatings, chewing gums, lozenges, breath fresheners, foams and sprays. These formulations may be used to treat natural or artificial tooth enamel, or any orally compatible material which is subject to mineral deposition. Although human use is preferred, use in animals is also possible.

The tartar barrier agents may be present in the formulations in effective concentrations generally in the range of from about 0.05 wt. % to as much as 30 wt. % or the limit of compatibility with a vehicle. A preferred concentration range for the agents of the formulations of the invention is from about 0.5 to about 10 wt. %. A more preferred range is from about 2 to about 8 wt. %.

The pH of these preparations should be between about pH 5 and 10, preferably between pH 5 and 8, more preferably between about 6 and 7.5. A pH lower than 5 is undesirable because of the possible enhancement of enamel demineralization.

Suitable conventional pharmaceutically acceptable vehicles that can be employed with the tartar barrier agents to prepare the compositions of this invention may comprise water, ethanol; such humectants as polypropylene glycol, glycerol and sorbitol; such gelling agents as cellulose derivatives, for example, Methocel carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example Cab-O-Sil M5, and polyvinylpyrrolidone; sweeteners such as sodium saccharin and aspartame; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the tartar barrier agent compositions of this invention.

| EXAMPLE A - Mouthwash Solution | |
|---|---|
| Tartar barrier agent | 0.5–2.0% w/w |
| Glycerol (Humectant) | 6.0 |
| Pluronic F-108 | 1.0 |
| Sodium saccharin (sweetener) | 0.3 |
| Deionized Water | q.s. |
| Flavors | 1.0 |
| | 100.0 |
| EXAMPLE B - Mouthwash Solution | |
| Tartar barrier agent | 0.5–3.0% w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |
| EXAMPLE C - Abrasive Dentifrice Gel | |
| Tartar barrier agent | 2.0–10.0% w/w |
| Fumed Silica (abrasive) | 55.0 |
| Sodium Lauryl Sulfate (detergent) | 1.5 |
| Glycerol (Humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.00 |
| EXAMPLE D - Chewing Gum | |
| Tartar barrier agent | 1.0–11.0% w/w |
| Gum Base | 21.3 |
| Sugar | 48.5–58.5 |
| Corn Syrup (Baume 45) | 18.2 |
| Flavors | 1.0 |
| | 100.00 |
| EXAMPLE E - Nonabrasive Gel Dentrifice | |
| Tartar barrier agent | 0.05–30.0% w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium saccharin | 0.2 |
| Flavors | 1.5 |
| | 100.0 |

In addition to the above materials which can be included in the present tartar barrier compositions, it is also contemplated to include therein a protease inhibitor to prevent the present peptides and polypeptides from being degraded by various proteolytic enzymes.

Examples of such inhibitors include aprotinin and trypsin inhibitor types I-P, I-S, II-L, II-O, II-S, II-T, III-O, and IV-O, although other inhibitors are within the scope of this invention. Similarly, when phosphopeptides are employed, it is contemplated to use phosphatase inhibitors in conjunction with the polypeptide to prevent or inhibit dephosphorylation of the polypeptides. Examples of such phosphatase inhibitors are sodium fluoride, adenosine diphosphate, and vinyl ether/maleic acid polymers (gantrez). Use of other phosphatase inhibitors is also possible.

The present peptides and polypeptides could also be linked to antibodies, particularly those against cavity-causing bacteria, or the antibodies could be added to a tartar barrier composition to enhance antibacterial activity.

The polypeptides of the present invention may also find suitable use in treatment and prevention of mineral buildups in arteries and veins, such as in atherosclerosis.

In this connection, the mode of administration of the polypeptides is preferably parenteral, i.e., intravenous, intraperitoneal, intramuscular, or subcutaneous, with intravenous administration being most preferred. They may be administered alone, without a carrier vehicle; however, they may also be administered with pharmaceutically acceptable nontoxic carriers, the proportions of which are determined by the suitability and chemical nature of the particular carrier. For intravenous or intramuscular administration, they may be used in the form of a sterile solution containing other solutes, for example, sufficient saline or glucose to make the solution isotonic. Like insulin, the peptides of the subject invention may also prove to be administrable by use of a continuous perfusion device, which should simplify the method of administration.

The physician will determine the dosage which will be most suitable for a particular situation. Dosages will generally depend upon the age and size of the patient, and the seriousness of the condition to be treated. A normal dosage will generally be in the range of 200-600 mg peptide per day.

The polypeptides of the present invention can also be used to impregnate prosthetic devices. For example, the polypeptides of the present invention could be incorporated into polymeric based (e.g. a copolymer of ethylene-vinyl acetate or a silicon rubber) controlled released drug delivery matrices for site specific therapy directly into the perianular region of the heart prosthesis (Levy, R. J. et al., CRC Critical Reviews in Biocompatibility 2, 148-187 (1986)). Controlled release devices incorporating a phosphonate derivative have been formulated to deliver that drug for more than 30 years without depletion. In addition, valve cusps could also be preloaded with a polypeptide according to the present invention via covalent aldehyde-amino linkages; such an approach could be useful as a primary anti-calcium measure or as an adjunct for priming controlled release anti-mineralization therapy.

The invention now being fully described, it will be apparent to one of ordinary skill in the art that many changes and modifications can be made thereto, without departing from the spirit or scope of the invention as set forth therein.

What is claimed as new and desired to be secured by letters patent of the United States is:

1. A poly-amino acid compound, which has the clustered polyanionic/clustered non-ionic partly hydrophobic structure:

where
each X is a residue independently selected from the group consisting of aspartic acid, glutamic acid, phosphoserine, phosphohomoserine, phosphotyrosine, and phosphothreonine,
each Y is independently a residue selected from the group consisting of alanine, leucine, isoleucine, valine and glycine,
n is 2 to 60,
m is 2 to 60, and
n+m ≧ 5,
and wherein poly $(X)_n$ may contain up to 10% of the Y residues and poly $(Y)_m$ may contain up to 10% of the X residues, and salts thereof.

2. A compound according to claim 1, in which the first X residue is at the N-terminal of said compound and the last Y residue is at the C-terminal of said compound.

3. A compound according to claim 1, in which the first X residue is at the C-terminal of said compound and the last Y residue is at the N-terminal of said compound.

4. A compound according to claim 1, having a formula selected from the group consisting of:

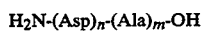

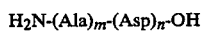

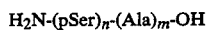

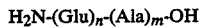

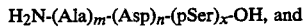

wherein:
n=10-60,
m=2-10, and
x=2-5.

5. A compound according to claim 4, which is: H$_2$N-(Ala)$_5$-(Asp)$_{18}$-(pSer)$_2$-OH.

6. A compound according to claim 4, which is: H$_2$N-(Ala)$_5$-(Asp)$_{15}$-OH.

7. A compound according to claim 4, which is: H$_2$N-(Ala)$_8$-(Asp)$_{40}$-OH.

8. A compound according to claim 1, wherein n=20-40, m=2-8, and the number of phosphorylated amino acids is 0-3.

9. A compound according to claim 1, wherein said aspartic acid and glutamic acid residues are in the form of sodium or potassium salts.

10. A compound according to claim 1, wherein said phosphoserine, phosphohomoserine, phosphotyrosine, and phosphothreonine residues are in the form of disodium, dipotassium, calcium or magnesium salts.

11. A method of inhibiting the deposition of a mineral on a surface other than a tooth, which comprises contacting said surface with a mineral deposition inhibiting effective amount of a compound according to claim 1.

12. A method according to claim 11, wherein said surface is of a prosthetic device for implantation in vivo.

13. A method according to claim 12, wherein said prosthetic device is a heart valve.

14. A method according to claim 11, wherein said compound is added to a liquid in contact with an industrial container.

15. A method according to claim 11, wherein said compound is coated on or impregnated into a surface which is ordinarily in contact with a marine environment.

16. An aqueous solution other than for oral use, comprising a crystallizable inorganic mineral, and a mineral crystallization inhibitory amount of a compound according to claim 1, wherein said inorganic mineral would crystallize in the absence of said compound.

* * * * *